(12) United States Patent
Nakajima et al.

(10) Patent No.: US 12,227,471 B2
(45) Date of Patent: Feb. 18, 2025

(54) POLYALKYLENE GLYCOL-BASED COMPOUND

(71) Applicant: IDEMITSU KOSAN CO., LTD., Chiyoda-ku (JP)

(72) Inventors: So Nakajima, Edogawa-ku (JP); Yukio Yoshida, Ichihara (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 558 days.

(21) Appl. No.: 17/418,080

(22) PCT Filed: Dec. 26, 2019

(86) PCT No.: PCT/JP2019/051167
§ 371 (c)(1),
(2) Date: Jun. 24, 2021

(87) PCT Pub. No.: WO2020/138309
PCT Pub. Date: Jul. 2, 2020

(65) Prior Publication Data
US 2022/0064093 A1 Mar. 3, 2022

(30) Foreign Application Priority Data
Dec. 28, 2018 (JP) .................. 2018-247425

(51) Int. Cl.
| | | |
|---|---|---|
| C07C 43/205 | (2006.01) | |
| C08G 65/04 | (2006.01) | |
| C10M 105/18 | (2006.01) | |
| C10M 107/34 | (2006.01) | |
| C10M 169/04 | (2006.01) | |
| C10N 20/02 | (2006.01) | |
| C10N 20/04 | (2006.01) | |
| C10N 40/16 | (2006.01) | |
| C10N 40/30 | (2006.01) | |

(52) U.S. Cl.
CPC .......... *C07C 43/2055* (2013.01); *C08G 65/04* (2013.01); *C10M 105/18* (2013.01); *C10M 107/34* (2013.01); *C10M 169/04* (2013.01); *C10M 2209/02* (2013.01); *C10M 2209/1045* (2013.01); *C10M 2209/1055* (2013.01); *C10M 2209/1065* (2013.01); *C10M 2209/1085* (2013.01); *C10N 2020/02* (2013.01); *C10N 2020/04* (2013.01); *C10N 2040/16* (2013.01); *C10N 2040/30* (2013.01)

(58) Field of Classification Search
None
See application file for complete search history.

(56) References Cited

U.S. PATENT DOCUMENTS

| | | | |
|---|---|---|---|
| 4,701,565 | A | 10/1987 | Satomura et al. |
| 6,189,322 | B1 | 2/2001 | Ishihara et al. |
| 2013/0109889 | A1 | 5/2013 | Arai et al. |
| 2022/0081513 | A1* | 3/2022 | Nakajima ............... C07C 43/15 |

FOREIGN PATENT DOCUMENTS

| | | |
|---|---|---|
| CN | 102959060 A | 3/2013 |
| EP | 2 586 853 A1 | 5/2013 |
| JP | 61-260036 A | 11/1986 |
| JP | 11-256177 A | 9/1999 |
| JP | 2000-212584 A | 8/2000 |
| JP | 2006-348059 A | 12/2006 |
| JP | 2011-195725 A | 10/2011 |
| JP | 2014-534316 A | 12/2014 |
| WO | WO 03/025033 A2 | 3/2003 |
| WO | WO 2011/162391 A1 | 12/2011 |

OTHER PUBLICATIONS

Copending U.S. Appl. No. 17/418,083, filed Jun. 24, 2021, which corresponds to US Patent Application Publication No. US 2022/0081513 A1. (Year: 2022).*

Extended European Search Report issued Aug. 22, 2022 in European Patent Application No. 19904081.7, citing documents 15-16 and 24-25 therein, 9 pages.

Renhua Shen, et al., "One-step synthesis of α-ρ-vinylphenylalkyl-ω-hydroxy poly(ethylene oxide) macromonomers by anionic polymerization initiated from ρ-vinylphenylalkanols," Polymer, vol. 44, XP004423193, 2003, pp. 3221-3228.

Mark P. Andrews, et al., "Reactions of Transition-Metal Atoms with Arenes, Arene-Functionalized Alkanes, Oligo(ethylene oxides), and Polysiloxanes," Inorganic Chemistry, vol. 25, No. 15, XP055950960, 1986, pp. 2587-2595.

(Continued)

*Primary Examiner* — Rosalynd A Keys
(74) *Attorney, Agent, or Firm* — Oblon, McClelland, Maier & Neustadt, L.L.P.

(57) ABSTRACT

A polyalkylene glycol-based compound may have formula (1):

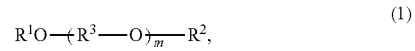

wherein $R^1$ is a monovalent aromatic hydrocarbon group having 6 to 42 ring carbon atoms; $R^2$ is a monovalent aromatic hydrocarbon group having 6 to 42 carbon atoms or a hydrogen atom; $R^3$ is a divalent hydrocarbon group having 2 to 4 carbon atoms; and m is a number in a range of from 1 to 40.

20 Claims, No Drawings

(56) References Cited

OTHER PUBLICATIONS

International Search Report issued on Feb. 10, 2020 in PCT/JP2019/051167 filed on Dec. 26, 2019, 3 pages.
Notice of Reasons for Refusal issued May 10, 2022 in Japanese Patent Application No. 2018-247425 (with English language translation), 8 pages.
Combined Chinese Office Action and Search Report issued Nov. 10, 2023 in Chinese Patent Application No. 201980086178.3 (with unedited computer-generated English translation), 23 pages.
Chinese Office Action mailed on Jun. 27, 2024, issued in Chinese Patent Application No. 201980086178.3, with English Translation, total 12 pages.
European Office Action mailed on Aug. 2, 2024 issued in European Patent Application 19904081.7, total 3 pages.
Chinese Office Action mailed on Sep. 13, 2024 issued in CN application 201980086178.3, with machine-generated English Translation, total 12 pages.
Office Action issued Dec. 5, 2024, in corresponding Korean Patent Application No. 10-2021-7019434 with English translation, 20 pages.

\* cited by examiner

POLYALKYLENE GLYCOL-BASED COMPOUND

CROSS-REFERENCE TO RELATED APPLICATIONS

The present application is the national stage of international application PCT/JP2019/051167, filed on Dec. 26, 2019, and claims the benefit of the filing date of Japanese Appl. No. 2018-247425, filed on Dec. 28, 2018.

TECHNICAL FIELD

The present invention relates to a polyalkylene glycol-based compound. In more detail, the present invention relates to a polyalkylene glycol-based compound and a lubricating oil composition containing the polyalkylene glycol-based compound.

BACKGROUND ART

As synthetic oils to be used for a lubricating oil composition, a polyalkylene glycol-based compound is known (see PTL 1). For example, for a car air conditioner of belt drive system which is mounted in a gasoline engine car or a diesel engine car, a lubricating oil composition using a polyalkylene glycol-based compound as the synthetic oil is broadly utilized.

CITATION LIST

Patent Literature

PTL 1: JP-T-2014-534316

SUMMARY OF INVENTION

Technical Problem

Now, hybrid cars and electric cars are becoming widespread recently. Following this, the car air conditioner which is mounted in a hybrid car or an electric car is also shifting from a belt drive system toward a motor drive system. In the car air conditioner of a motor drive system (car air conditioner of a motor drive system in which an electric compressor and a motor are integrated), the motor is dipped in a lubricating oil composition, and therefore, a winding for motor comes into direct contact with the lubricating oil composition. Then, the foregoing lubricating oil composition is required to be excellent in electric insulation.

However, the conventional polyalkylene glycol-based compounds are not satisfactory in the electric insulation.

An object of the present invention is to provide a polyalkylene glycol-based compound which is excellent in electric insulation.

Solution to Problem

The present inventors have found that a polyalkylene glycol-based compound having a specified structure is excellent in electric insulation, thereby leading to accomplishment of the present invention.

Specifically, the present invention relates to the following [1] to [6].

[1] A polyalkylene glycol-based compound represented by the following general formula (1):

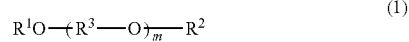

wherein $R^1$ represents a monovalent aromatic hydrocarbon group having 6 to 42 ring carbon atoms; $R^2$ represents a monovalent aromatic hydrocarbon group having 6 to 42 ring carbon atoms or a hydrogen atom; $R^3$ represents a divalent hydrocarbon group having 2 to 4 carbon atoms; and m is a number of 1 to 40.

[2] The polyalkylene glycol-based compound as set forth in the above [1], wherein the monovalent aromatic hydrocarbon group is a group selected from the following general formulae (2) to (7):

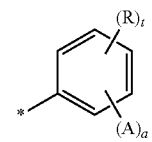

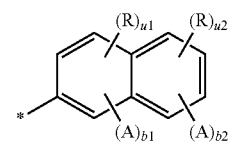

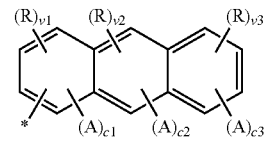

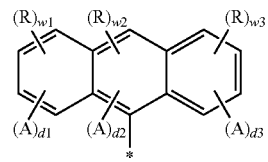

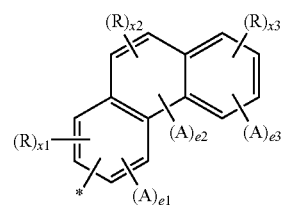

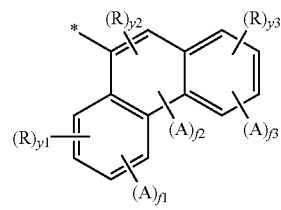

wherein R's are each independently a methyl group, an ethyl group, or a vinyl group; and A's each independently represent a group represented by the following general formula (8):

(8)

wherein,
in the general formula (2), t is an integer of 0 to 5; and a is an integer of 0 to 2, with proviso of (t+a)≤5;
in the general formula (3), (u1+u2) is an integer of 0 to 7; and (b1+b2) is an integer of 0 to 2, with proviso of (u1+u2+b1+b2)≤7;
in the general formula (4), (v1+v2+v3) is an integer of 0 to 9; and (c1+c2+c3) is an integer of 0 to 2, with proviso of (v1+v2+v3+c1+c2+c3)≤9;
in the general formula (5), (w1+w2+w3) is an integer of 0 to 9; and (d1+d2+d3) is an integer of 0 to 2, with proviso of (w1+w2+w3+d1+d2+d3)≤9;
in the general formula (6), (x1+x2+x3) is an integer of 0 to 9; and (e1+e2+e3) is an integer of 0 to 2, with proviso of (x1+x2+x3+e1+e2+e3)≤9;
in the general formula (7), (y1+y2+y3) is an integer of 0 to 9; and (f1+f2+f3) is an integer of 0 to 2, with proviso of (y1+y2+y3+f1+f2+f3)≤9;
in the general formulae (2) to (7), * represents a bonding position to the oxygen atom in the general formula (1); and
in the general formula (8), z is an integer of 0 to 2; $L^1$ is a vinylene group; and $Ar^1$ is one kind selected from the general formulae (2) to (7) (however, when one kind selected from the general formulae (2) to (7) is $Ar^1$, then * represents a bonding position to $L^1$ in the general formula (8)).
[3] The polyalkylene glycol-based compound as set forth in the above [1] or [2], wherein a hydroxyl value is 60 mgKOH/g or less.
[4] The polyalkylene glycol-based compound as set forth any one of the above [1] to [3], wherein a volume resistivity at 25° C. is 0.0030 TΩ·m or more.
[5] A lubricating oil composition including the polyalkylene glycol-based compound as set forth in any one of the above [1] to [4].
[6] The lubricating oil composition as set forth in the above [5], further including at least one additive selected from an antioxidant, an oiliness improver, an oxygen scavenger, an extreme pressure agent, a copper deactivator, a rust inhibitor, an anti-foaming agent, and a viscosity index improver.

Advantageous Effects of Invention

In accordance with the present invention, it is possible to provide a polyalkylene glycol-based compound which is excellent in electric insulation.

DESCRIPTION OF EMBODIMENTS

[Polyalkylene Glycol-Based Compound]
The polyalkylene glycol-based compound of the present invention is represented by the following general formula (1).

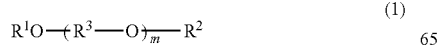
(1)

In the general formula (1). $R^1$ represents a monovalent aromatic hydrocarbon group having 6 to 42 ring carbon atoms; $R^2$ represents a monovalent aromatic hydrocarbon group having 6 to 42 ring carbon atoms or a hydrogen atom; $R^3$ represents a divalent hydrocarbon group having 2 to 4 carbon atoms; and m is a number of 1 to 40.

The polyalkylene glycol-based compound represented by the general formula (1) is high in volume resistivity and excellent in electric insulation.

In this specification, among the compounds represented by the general formula (1), one in which $R^2$ is a hydrogen atom is occasionally referred to as "one-end blocked polyalkylene glycol-based compound"). In addition, among the compounds represented by the general formula (1), one in which $R^2$ is not a hydrogen atom is occasionally referred to as "both-end blocked polyalkylene glycol-based compound".

The polyalkylene glycol-based compound may be a "one-end blocked polyalkylene glycol-based compound" alone, may be a "both-end blocked polyalkylene glycol-based compound" alone, or may be a mixture of a "one-end blocked polyalkylene glycol-based compound" and a "both-end blocked polyalkylene glycol-based compound". In the present invention, these are named generically as "polyalkylene glycol-based compound". In addition, in this specification, the "polyalkylene glycol-based compound" is also occasionally abbreviated as "PAG".

From the viewpoint of more improving the volume resistivity of the PAG, the polyalkylene glycol-based compound according to an embodiment of the present invention is preferably a "both-end blocked polyalkylene glycol-based compound" alone, or a mixture of a "one-end blocked polyalkylene glycol-based compound" and a "both-end blocked polyalkylene glycol-based compound"; and more preferably a "both-end blocked polyalkylene glycol-based compound" alone.

$R^1$, $R^2$, $R^3$, and m in the general formula (1) are hereunder described in detail.

<$R^1$ and $R^2$>

In the general formula (1), $R^1$ represents a monovalent aromatic hydrocarbon group having 6 to 42 ring carbon atoms.

In the general formula (1), $R^2$ represents a monovalent aromatic hydrocarbon group having 6 to 42 ring carbon atoms or a hydrogen atom.

$R^1$ and $R^2$ may be the same as or different from each other.
(Monovalent Aromatic Hydrocarbon Group Having 6 to 42 Ring Carbon Atoms)

The monovalent aromatic hydrocarbon group having 6 to 42 ring carbon atoms, which is selected as $R^1$ and $R^2$, is, for example, selected from the following general formulae (2) to (7).

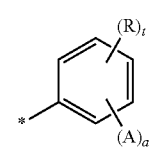
(2)

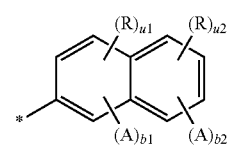
(3)

-continued

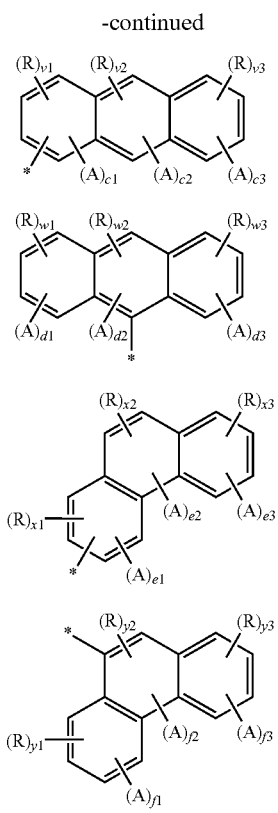

In the general formulae (2) to (7), R's are each independently a methyl group, an ethyl group, or a vinyl group; and A's each independently represent a group represented by the following general formula (8).

$$\text{———}(\text{L}^1)_{\overline{z}}\text{—Ar}^1 \quad (8)$$

In the general formula (2), t is an integer of 0 to 5; and a is an integer of 0 to 2, with proviso of (t+a)≤5.

In the general formula (3), (u1+u2) is an integer of 0 to 7; and (b1+b2) is an integer of 0 to 2, with proviso of (u1+u2+b1+b2)≤7.

In the general formula (4), (v1+v2+v3) is an integer of 0 to 9; and (c1+c2+c3) is an integer of 0 to 2, with proviso of (v1+v2+v3+c1+c2+c3)≤9.

In the general formula (5), (w1+w2+w3) is an integer of 0 to 9; and (d1+d2+d3) is an integer of 0 to 2, with proviso of (w1+w2+w3+d1+d2+d3)≤9.

In the general formula (6), (x1+x2+x3) is an integer of 0 to 9; and (e1+e2+e3) is an integer of 0 to 2, with proviso of (x1+x2+x3+e i+e2+e3)≤9.

in the general formula (7), (y1+y2+y3) is an integer of 0 to 9; and (f1+f2+f3) is an integer of 0 to 2, with proviso of (y1+y2+y3+f1+f2+f3)≤9;

In the general formulae (2) to (7), * represents a bonding position to the oxygen atom in the general formula (1).

In the general formula (8), z is an integer of 0 to 2; $L^1$ is a vinylene group; and $Ar^1$ is one kind selected from the general formulae (2) to (7) (however, when one kind selected from the general formulae (2) to (7) is $Ar^1$, then * represents a bonding position to $L^1$ in the general formula (8)).

In this specification, the number of ring carbon atoms of the aromatic hydrocarbon group which is selected as $R^1$ and $R^2$ expresses the number of carbon atoms constituting the foregoing ring itself of the compound of a structure in which the carbon atoms are bonded in a ring form. In the case where the foregoing ring is substituted with a substituent, when the substituent is an aromatic hydrocarbon group, the carbon number of the foregoing aromatic hydrocarbon group is included in the number of ring carbon atoms, too.

In the general formulae (2) to (7), the solid lines from the substituents R and A toward the aromatic ring express single bonds of the substituents R and A to the carbon atoms constituting the aromatic ring and mean that the substituents R and A may be bonded to the carbon atoms constituting the aromatic ring at arbitrary positions, respectively.

As for the conventional PAG's, the terminals were constituted of a hydroxy group, a methyl group, a butyl group, and the like. However, in this case, the volume resistivity of the PAG is liable to become low. For that reason, in a car air conditioner of a motor drive system (car air conditioner of a motor drive system in which an electric compressor and a motor are integrated), there is a concern that when a lubricating oil composition constituted of the PAG comes into direct contact with a winding for motor, a risk for safety could be caused due to an electric leakage or the like.

In contrast, as in the present invention, in the general formula (1), when $R^1$ is a monovalent aromatic hydrocarbon group having 6 to 42 ring carbon atoms, and $R^2$ is a monovalent aromatic hydrocarbon group having 6 to 42 ring carbon atoms or a hydrogen atom, the volume resistivity of the PAG is enhanced, whereby the electric insulation can be made excellent, and a risk for safety to be caused due to an electric leakage, or the like can be inhibited. In consequence, it becomes possible to use the PAG as the lubricating oil composition in a car air conditioner of a motor drive system.

With respect to the case where a, b1, b2, c1, c2, c3, d1, d2, d3, e1, e2, e3, f1, f2, and f3 are 0, first of all, preferred embodiments regarding $R^1$ and $R^2$ are hereunder described on the basis of the general formulae (2) to (7).

(Case where a, b1, b2, c1, c2, c3, d1, d2, d3, e1, e2, e3, f1, f2, and f3 are 0)

In the group represented by the general formula (2), t is preferably 0 to 2, more preferably 0 to 1, and still more preferably 0 (namely, unsubstituted). R is preferably a methyl group or a vinyl group.

Specific examples of the group represented by the general formula (2) include a phenyl group, a tolyl group, a dimethylphenyl group, and styryl group. Of these, a phenyl group, a tolyl group, and a styryl group are preferred, and a phenyl group is more preferred.

In the compound of the general formula (3), (u1+u2) is preferably 0 to 4, more preferably 0 to 2, still more preferably 0 to 1, and yet still more preferably 0 (namely, unsubstituted). In addition, R is preferably a methyl group or a vinyl group.

Specific examples of the group represented by the general formula (3) include a naphthyl group, a methylnaphthyl group, a dimethylnaphthyl group, and a vinylnaphthyl group. Of these, a naphthyl group, a methylnaphthyl group, and a vinylnaphthyl group are preferred, and a naphthyl group is more preferred.

In the compounds of the general formulae (4) and (5), (v1+v2+v3) and (w1+w2+w3) are preferably 0 to 5, more preferably 0 to 3, still more preferably 0 to 2, yet still more preferably 0 to 1, and even yet still more preferably 0 (namely, unsubstituted). In addition, R is preferably a methyl group or a vinyl group.

Specific examples of the groups represented by the general formulae (4) and (5) include an anthracenyl group, a methylanthracenyl group, a dimethylanthracenyl group, and a vinylanthracenyl group. Of these, an anthracenyl group, a methylanthracenyl group, and a vinylanthracenyl group are preferred, and an anthracenyl group is more preferred.

In the compounds of the general formulae (6) and (7), (x1+x2+x3) and (y1+y2+y3) are preferably 0 to 5, more preferably 0 to 3, still more preferably 0 to 2, yet still more preferably 0 to 1, and even yet still more preferably 0 (namely, unsubstituted). In addition, R is preferably a methyl group or a vinyl group.

Specific examples of the groups represented by the general formulae (6) and (7) include a phenanthrenyl group, a methylphenanthrenyl group, a dimethylphenanthrenyl group, and a vinylphenanthrenyl group. Of these, a phenanthrenyl group, a methylphenanthrenyl group, and vinylphenanthrenyl group are preferred, and a phenanthrenyl group is more preferred.

In the general formulae (2) to (7), when plural R's exist, the respective R's may be the same as or different from each other.

Next, with respect to the case where a, b1, b2, c1, c2, c3, d1, d2, d3, e1, e2, e3, f1, f2, and f3 are not 0, preferred embodiments regrading $R^1$ and $R^2$ are described on the basis of the general formulae (2) to (8).

(Case where a, b1, b2, c1, c2, c3, d1, d2, d3, e1, e2, e3, f1, f2, and f3 are not 0)

In the general formula (8), though z is preferably 0 (namely, it is meant that the carbon atoms constituting the aromatic ring of the general formulae (2) to (7) are bonded directly to $Ar^1$) or 1, it is more preferably 1.

In the general formulae (2) to (7), the total number of the substituents A (namely, a, (b1+b2), (c1+c2+c3), (d1+d2+d3), (e1+e2+e3), and (f1+f2+f3)) is 1 or 2.

In the case where the general formulae (2) to (7) have the substituent R, the group represented by the general formula (2) or (3) is preferred, and the group represented by the general formula (2) is more preferred. $Ar^1$ is preferably the group represented by the general formula (2) or (3), and more preferably the group represented by the general formula (2).

In the general formulae (2) to (7), when plural A's exist, the respective R's may be the same as or different from each other.

In the general formula (8), the general formulae (2) to (7) as $Ar^1$ may have a substituent A. The foregoing substituent A is also represented by the general formula (8), and preferred examples of $L^1$ and $Ar^1$ are also the same as those mentioned above.

When the general formulae (2) to (7) have the substituent A, preferred specific examples thereof include a biphenyl group, a binaphthyl group, and a group derived from distyrylbenzene. Of these, a group derived from distyrylbenzene is preferred. The "group derived from distyrylbenzene" means a group in which in distyrylbenzene, the hydrogen atom is eliminated at a position serving as a bonding point to the oxygen atom in the general formula (1). The bonding point may be the carbon atom in the central benzene ring of distyrylbenzene or may be the carbon atom of the end benzene ring.

Even in the case where a, b1, b2, c1, c2, c3, d1, d2, d3, e1, e2, e3, f1, f2, and f3 are not 0, the substituent R may exist in the general formulae (2) to (7). In this case, the total number of the substituents R (t, (u1+u2), (v1+v2+v3), (w1+w2+w3), (x1+x2+x3)), and (y1+y2+y3) and the kinds thereof are the same as those mentioned above.

((Preferred Substituent Selected as $R^1$ and $R^2$))

The substituents which are selected as $R^1$ and $R^2$ are each independently preferably a monovalent aromatic hydrocarbon group having 6 to 42 ring carbon atoms. The number of ring carbon atoms of the aromatic hydrocarbon group is preferably 6 to 30, more preferably 6 to 24, and still more preferably 6 to 20.

At least one of $R^1$ and $R^2$ is preferably the group represented by the general formula (2). In addition, as for the group represented by the general formula (2), t is preferably 0. In the case where the group represented by the general formula (2) has A, a is preferably 2, z is preferably 1, and $Ar^1$ is preferably the group represented by the general formula (2). Alternatively, a is preferably 1, z is preferably 1, and $Ar^1$ is preferably the group represented by the general formula (2), and the general formula (2) as $Ar^1$ may have A.

That is, it is preferred that at least one of $R^1$ and $R^2$ is a phenyl group or a group derived from distyrylbenzene; it is preferred that both of them are a phenyl group or a group derived from distyrylbenzene; it is more preferred that one of them is a phenyl group, and the other is a group derived from distyrylbenzene; and it is still more preferred that both of them are a group derived from distyrylbenzene.

<$R^3$ and m>

In the general formula (1), $R^3$ represents a divalent hydrocarbon group having 2 to 4 carbon atoms.

Examples of the divalent hydrocarbon group having 2 to 4 carbon atoms, which may be selected as $R^3$, include an ethylene group, various propylene groups (a n-propylene group, an isopropylene group, and a cyclopropylene group), and various butylene groups (a n-butylene group, a sec-butylene group, an isobutylene group, a tert-butylene group, and a cyclobutylene group).

The number of m is an average value of the number of the ($R^3O$) unit and is also an average addition molar number of the ($R^3O$) unit.

In the case where plural ($R^3O$) units exist, namely, in the case of m≥2, the respective ($R^3O$) units may be the same as or different from each other.

In the case where the respective ($R^3O$) units are different from each other, the respective ($R^3O$) units may be subjected to random addition or may be subjected to block addition. However, the random addition is preferred from the viewpoint of handling properties.

From the viewpoint of improving the volume resistivity of the PAG, the divalent hydrocarbon group having 2 to 4 carbon atoms, which may be selected as $R^3$, is preferably a divalent hydrocarbon having 4 carbon atoms (namely, various butylene groups). In addition, in the case of m≥2, a proportion of the ($R^3O$) unit in which $R^3$ is constituted of a divalent hydrocarbon group having 4 carbon atoms and which occupies relative to the whole amount of the ($R^3O$) unit is preferably 0.5 or more, more preferably 0.6 or more, still more preferably 0.7 or more, yet still more preferably 0.8 or more, even yet still more preferably 0.9 or more, and even still more preferably 1.0 in terms of a molar ratio.

The number of m is 1 to 40, and from the viewpoint of more improving the volume resistivity of the PAG, it is preferably 5 to 35, more preferably 5 to 30, still more preferably 5 to 20, and yet still more preferably 5 to 15.

[Physical Properties of Polyalkylene Glycol-Based Compound]

The volume resistivity, the hydroxyl value, the mass average molecular weight, the number average molecular weight, the 40° C. kinematic viscosity, the 100° C. kinematic viscosity, and the viscosity index of the polyalkylene glycol-based compound according to an embodiment of the present invention are hereunder described.

<Volume Resistivity>

The volume resistivity at 25° C. of the PAG according to an embodiment of the present invention is preferably 0.0030 TΩ·m or more, more preferably 0.0050 TΩ·m or more, still more preferably 0.0100 TΩ·m or more, yet still more preferably 0.0200 TΩ·m or more, even yet still more preferably 0.0400 TΩ·m or more, even still more preferably 0.0600 TΩ·m or more, and even still more further preferably 0.0800 TΩ·m or more, and it is typically 1 TΩ·m or less.

In this specification, the volume resistivity at 25° C. is a value obtained through measurement at room temperature (25° C.) in conformity with JIS C2101-24 (volume resistivity test).

<Hydroxyl Value>

From the viewpoint of more improving the volume resistivity, the hydroxyl value of the PAG according to an embodiment of the present invention is preferably 60 mgKOH/g or less, more preferably 50 mgKOH/g or less, still more preferably 40 mgKOH/g or less, yet still more preferably 30 mgKOH/g or less, even yet still more preferably 20 mgKOH/g or less, and even still more preferably 10 mgKOH/g or less. So far as the hydroxyl value is 60 mgKOH/g or less, the PAG in which the both ends are not blocked does not substantially exist in the mixture. Then, as the hydroxyl value becomes smaller than this value, the proportion at which the "both-end blocked polyalkylene glycol-based compound" occupies in the mixture of the "one-end blocked polyalkylene glycol-based compound" and the "both-end blocked polyalkylene glycol-based compound" increases, and the volume resistivity of the PAG is improved.

In this specification, the hydroxyl value is a value through measurement by the neutralization titration method in conformity with JIS K0070

<Mass Average Molecular Weight (Mw) and Number Average Molecular Weight (Mn)>

The mass average molecular weight (Mw) of the polyalkylene glycol-based compound according to an embodiment of the present invention is preferably 500 to 5,000, more preferably 700 to 3,000, and still more preferably 800 to 2,000.

The number average molecular weight (Mn) of the polyalkylene glycol-based compound according to an embodiment of the present invention is preferably 500 to 5,000, more preferably 600 to 2,500, and still more preferably 700 to 1,800.

The mass average molecular weight (Mw) and the number average molecular weight (Mn) can be measured by the method described in the section of Examples as mentioned later.

<40° C. Kinematic Viscosity, 100° C. Kinematic Viscosity, and Viscosity Index>

The 40° C. kinematic viscosity of the polyalkylene glycol-based compound according to an embodiment of the present invention is preferably 10 to 400 mm$^2$/s, more preferably 20 to 300 mm$^2$/s, still more preferably 20 to 200 mm$^2$/s, and yet still more preferably 30 to 100 mm$^2$/s.

The 100° C. kinematic viscosity of the polyalkylene glycol-based compound according to an embodiment of the present invention is preferably 2.0 to 30 mm$^2$/s, more preferably 3.0 to 25 mm$^2$/s, still more preferably 4.0 to 20 mm$^2$/s, and yet still more preferably 5.0 to 18 mm$^2$/s.

The viscosity index of the polyalkylene glycol-based compound according to an embodiment of the present invention is preferably 70 to 250, more preferably 80 to 230, and still more preferably 90 to 220.

The 40° C. kinematic viscosity, the 100° C. kinematic viscosity, and the viscosity index are each a value measured and calculated by using a glass-made capillary viscometer in conformity with JIS K2283-2000.

[Production Method of Polyalkylene Glycol-Based Compound]

The production method of the polyalkylene glycol-based compound of the present invention is not particularly limited.

As for the production method of the polyalkylene glycol-based compound according to an embodiment of the present invention, the one-end blocked polyalkylene glycol-based compound can be produced by addition-polymerizing an oxirane monomer in the presence of an alkali metal alkoxide and then removing the alkali metal ion. In the case of introducing the group having the substituent A, such as a group derived from distyrylbenzene, a compound in which a hydroxyl group is introduced into the compound serving as a constituent source of the substituent A may be used in combination with the alkali metal alkoxide, such as sodium methoxide. For example, in the case of introducing a group derived from distyrylbenzene as the substituent A, a compound having a hydroxyl group added to a benzene ring of trans, trans-1-styryl-4-styryl may be used in combination.

The alkali metal alkoxide is obtained through alkoxylation of an alcohol with a hydride of an alkaline metal. The alcohol to be used is changed according to R$^1$ of the general formula (1). As the alkali metal, at least one selected from sodium, potassium, and the like is used, with sodium being preferred.

As the oxirane monomer, at least one selected from ethylene oxide, propylene oxide, and butylene oxide is used. Of these, from the viewpoint of more improving the volume resistivity of the PAG, butylene oxide is preferably used, and in the case where a combination of butylene oxide with ethylene oxide and/or propylene oxide is used as the oxirane monomer, the proportion at which the butylene oxide occupies relative to the whole amount of the oxirane monomer is preferably 0.5 or more, more preferably 0.6 or more, still more preferably 0.7 or more, yet still more preferably 0.8 or more, and even yet still more preferably 0.9 or more in terms of a molar ratio.

On the occasion of addition-polymerizing the oxirane monomer in the presence of an alkali metal alkoxide, for example, the reaction temperature is 85 to 125° C., the reaction time is 8 to 24 hours, and the reaction pressure is 0.1 to 3 MPa.

Examples of a method for removing the alkali metal ion from the reaction product include a method of using an ion exchange resin. Specifically, there is exemplified a method in which a solution in which the reaction product is dissolved in a mixed solvent of water and methanol is passed through a column having a cation exchange resin filled therein and then passed through a column having an anion exchange resin filled therein.

Thereafter, by removing the mixed solvent by means of distillation or the like, the one-end blocked polyalkylene glycol-based compound can be produced.

The both-end blocked polyalkylene glycol-based compound is obtained by reacting the one-end blocked polyalkylene glycol compound with an alkali metal compound, such as sodium methoxide, to substitute the hydrogen atom of the hydroxyl group with the alkali metal and subsequently, reacting this with a compound represented by the following general formula (9) to substitute the alkali metal moiety with $R^2$.

In the general formula (9), X is at least one selected from a fluorine atom, a chlorine atom, a bromine atom, and an iodine atom; and $R^2$ is the same as that in the general formula (1) (provided that a hydrogen atom is excluded).

On the occasion of reacting the one-end blocked polyalkylene glycol compound with the alkali metal compound, such as sodium methoxide, for example, the reaction temperature is 20 to 60° C., the reaction time is 1 to 2 hours, and the reaction pressure is 0.1 to 1 MPa.

On the occasion of reacting the one-end blocked polyalkylene glycol compound with the alkali metal compound, such as sodium methoxide and then reacting with the compound represented by the general formula (2) to substitute the alkali metal moiety with $R^2$, for example, the reaction temperature is 60 to 90° C., the reaction time is 8 to 24 hours, and the reaction pressure is 0.1 to 1 MPa.

Examples of a method for removing an alkali metal halide from the reaction product include a method in which a solution in which the reaction product is dissolved in a mixed solvent of water and methanol is passed through a column having a cation exchange resin filled therein and then passed through a column having an anion exchange resin filled therein.

Thereafter, by removing the mixed solvent by means of distillation or the like, the both-end blocked polyalkylene glycol-based compound can be produced.

In the reaction product, the proportion at which the both-end blocked polyalkylene glycol-based compound occupies relative to the total amount of the one-end blocked polyalkylene glycol-based compound and the both-end blocked polyalkylene glycol-based compound can be regulated by the blending amount of the alkali metal compound, such as sodium methoxide, relative to the one-end blocked polyalkylene glycol compound on the occasion of reacting the one-end blocked polyalkylene glycol compound with the alkali metal compound, the blending amount of the compound represented by the general formula (1) relative to the one-end blocked polyalkylene glycol compound, the reaction time, the reaction temperature, the reaction pressure, and so on.

[Lubricating Oil Composition]

The lubricating oil composition of the present invention contains the aforementioned PAG. In view of the fact that the lubricating oil composition contains the PAG, the electric insulation is improved.

In the lubricating oil composition, the content of the PAG is typically 50 to 100% by mass, preferably 60 to 100% by mass, more preferably 70 to 100% by mass, yet still more preferably 80 to 100% by mass, and even yet still more preferably 90 to 100% by mass on the basis of the whole amount (100% by mass) of the lubricating oil composition.

The lubricating oil composition may further contain at least one additive selected from an antioxidant, an oiliness improver, an oxygen scavenger, an extreme pressure agent, a copper deactivator, a rust inhibitor, an anti-foaming agent, and a viscosity index improver within the range that does not hinder the effect of the PAG.

The lubricating oil composition may be one composed of only the PAG according to an application.

<Lubricating Oil Composition for Refrigerator>

The lubricating oil composition is preferably used as a lubricating oil composition for refrigerator (hereinafter also referred to as "refrigerator oil"). That is, the foregoing refrigerator oil is used upon being filled together with a refrigerant in the interior of a refrigerator, and for example, it is used for lubricating a sliding part of a compressor provided in the refrigerator, or the like. In the following description, the mixture of the refrigerator oil and the refrigerant is also referred to as a "refrigerator oil composition".

In view of the fact that the refrigerator oil containing the PAG is excellent in electric insulation, a risk for safety to be caused due to an electric leakage, or the like can be inhibited. In consequence, the refrigerator oil is preferably used as a refrigerator oil in a car air conditioner of a motor drive system. As a matter of course, the refrigerator oil can also be used in a car air conditioner of a belt drive system, an air-conditioning machine, an icebox, an automatic vending machine, a showcase, a refrigeration system, a hot water supplying system, or a heating system, other than the car air conditioner of a motor drive system.

As the refrigerant which is used upon being mixed with the refrigerator oil, there is exemplified at least one selected from an unsaturated fluorinated hydrocarbon compound (hereinafter also referred to as "HFO refrigerant"), a saturated fluorinated hydrocarbon compound (hereinafter also referred to as "HFC refrigerant"), a hydrocarbon-based refrigerant (hereinafter also referred to as "HC refrigerant"), carbon dioxide, and ammonia. Of these, a refrigerant including an HFO refrigerant is preferably used.

(HFO Refrigerant)

Examples of the HFO refrigerant include compounds having a carbon-carbon double bond, such as fluorides of a linear or branched chained olefin having 2 or more and 6 or less carbon atoms; and a cyclic olefin having 4 or more and 6 or less carbon atoms.

More specifically, examples thereof include an ethylene having 1 or more and 3 or less (preferably 3) fluorine atoms introduced thereinto; a propene having 1 or more and 5 or less fluorine atoms introduced thereinto; a butene having 1 or more and 7 or less fluorine atoms introduced thereinto; a pentene having 1 or more and 9 or less fluorine atoms introduced thereinto; a hexene having 1 or more and 11 or less fluorine atoms introduced thereinto; a cyclobutene having 1 or more and 5 or less fluorine atoms introduced thereinto; a cyclopentene having 1 or more and 7 or less fluorine atoms introduced thereinto; and a cyclohexene having 1 or more and 9 or less fluorine atoms introduced thereinto.

Of these HFO refrigerants, a fluoride of a propene is preferred, a propene having 3 or more and 5 or less fluorine atoms introduced thereinto is more preferred, and a propene having 4 fluorine atoms introduced thereinto is still more preferred.

Suitable examples of the HFO refrigerant include 1,2,3,3,3-pentafluoropropene (R1225ye), 2,3,3,3-tetrafluoropropene (R1234yf), 1,3,3,3-tetrafluoropropene (R1234ze), 1,2,3,3-tetrafluoropropene (R1234yz), 1,1,2-trifluoroethylene (R1123), and (Z)-1,1,1,4,4,4-hexafluoro-2-butene (R1336mzz(Z)). Of these HFO refrigerants, at least one selected from the group consisting of R1234yf, R1234ze, R1123, and R1336mzz(Z) is preferred; at least one selected from the group consisting of R1234yf, R1234ze, and R1336mzz(Z) is more preferred; and at least one selected from the group consisting of R1234yf and R1234ze is still more preferred.

(HFC Refrigerant)

The HFC refrigerant is preferably a fluoride of an alkane having 1 or more and 4 or less carbon atoms, more preferably a fluoride of an alkane having 1 or more and 3 or less carbon atoms, and still more preferably a fluoride of an alkane having 1 or 2 carbon atoms (methane or ethane). Examples of the fluoride of methane or ethane include trifluoromethane (R23), difluoromethane (R32), 1,1-difluoroethane (R152a), 1,1,1-trifluoroethane (R143a), 1,1,2-trifluoroethane (R143), 1,1,1,2-tetrafluoroethane (R134a), 1,1,2,2-tetrafluoroethane (R134), and 1,1,1,2,2-pentafluoroethane (R125). Of these HFC refrigerants, at least one selected from the group consisting of R32, R134a, and R125 is preferred, and R32 is more preferred.

(HC Refrigerant)

The hydrocarbon-based refrigerant is preferably a hydrocarbon having 1 or more and 8 or less carbon atoms, more preferably a hydrocarbon having 1 or more and 5 or less carbon atoms, and still more preferably a hydrocarbon having 3 or more and 5 or less carbon atoms. When the carbon number is 8 or less, a boiling point of the refrigerant does not become excessively high, and hence, such is preferred as the refrigerant. As the hydrocarbon-based refrigerant, there is exemplified at least one selected from the group consisting of methane, ethane, ethylene, propane (R290), cyclopropane, propylene, n-butane, isobutane (R600a), 2-methylbutane, n-pentane, isopentane, cyclopentane, isobutane, and n-butane.

(Content Ratio of Refrigerator Oil and Refrigerant)

In the refrigerator oil composition, a content ratio of the refrigerator oil and the refrigerant ((refrigerator oil)/refrigerant) is preferably 1/99 to 99/1, more preferably 1/99 to 90/10, still more preferably 5/95 to 70/30, and yet still more preferably 5/95 to 60/40 in terms of a mass ratio. By controlling the content ratio of the refrigerator oil and the refrigerant to the aforementioned range, lubricity and suitable refrigeration ability in the refrigerator are exhibited.

(Moisture Content in Refrigerator Oil Composition)

The moisture content of the refrigerator oil composition according to an embodiment of the present invention is preferably 800 ppm by mass or less, more preferably 700 ppm by mass or less, still more preferably 500 ppm by mass or less, and yet still more preferably 300 ppm by mass or less. In the refrigerator oil composition according to an embodiment of the present invention, though a lower limit value of the moisture content is not particularly limited, it is preferably 50 ppm by mass or more.

(Other Application of Lubricating Oil Composition)

The lubricating oil composition may also be used for a transmission, a shock absorber, various gear apparatuses, various bearing mechanisms, other various industrial apparatuses, and so on, other than the refrigerator application.

(Apparatus)

As the apparatus according to an embodiment of the present invention, there is exemplified at least one selected from a car air conditioner of a motor drive system (car air conditioner of a motor drive system in which an electric compressor and a motor are integrated), a car air conditioner of a belt drive system, an air-conditioning machine, a refrigerator, an automatic vending machine, a showcase, a refrigeration system, a hot water supplying system, and a heating system, each having the lubricating oil composition filled therein.

In addition, examples of the apparatus according to an embodiment of the present invention include an industrial apparatus having the lubricating oil composition filled therein. As the industrial apparatus, there is exemplified at least one selected from a transmission, a shock absorber, various gear structures, and various bearing mechanisms.

EXAMPLES

The present invention is hereunder specifically described by reference to Examples, but it should be construed that the present invention is not limited to the following Examples.

PRODUCTION EXAMPLES

PAG's were prepared by the following Production Examples.

Production Example A1

(Step A1-1)

A 200 mL-volume stainless steel-made autoclave installed with a stirrer and a liquid-introducing tube (hereinafter also referred to simply as "autoclave") was charged with 6.4 g (0.056 mol) of sodium phenoxide and then hermetically sealed. Then, an autoclave temperature was raised to 105° C., and 77 g (1.32 mol) of propylene oxide was injected into the autoclave from the liquid-introducing tube under stirring over 9 hours, to obtain a reaction product. The reaction product was subjected to temperature lowering to room temperature (25° C.), and this was then dissolved in 100 mL of water and 200 mL of methanol, to prepare a solution of the reaction product. The foregoing solution was passed through a column having 200 mL of a cation exchange resin filled therein and then passed through a column having 200 mL of an anion exchange resin filled therein, to remove the sodium ion from the reaction product. Subsequently, the methanol and water were distilled off from the solution after passing through the columns, and the residue was dried under reduced pressure with a vacuum pump (0.4 mmHg) at 100° C. for 1 hour, to obtain 91 g of a one-end blocked polyalkylene glycol-based compound A1 ($R^1$=phenyl group, $R^2$=H, $R^3$=propylene group (monomer: propylene oxide (PO), hereinafter also referred to as "C3"), m=16).

(Step A1-2)

In a 300 mL-volume glass-made three-necked flask installed with a stirrer and a distillation head (hereinafter also referred to simply as "flask"), 50 g of the one-end blocked polyalkylene glycol-based compound A1 obtained in Step A1-1 and 80 mL of toluene were charged and then stirred while heating to distill off about 20 mL of the toluene, thereby removing the moisture remained in the charged one-end blocked polyalkylene glycol-based compound A1. Subsequently, after temperature lowering to room temperature (25° C.), 25 g of a methanol solution of sodium methoxide (sodium methoxide concentration: 28% by mass) (sodium methoxide: 0.13 mol) was charged in the flask and heated to distill off the methanol and about 20 mL of the toluene.

After temperature lowering to room temperature (25° C.), the contents in the flask were transferred into the autoclave, and the autoclave was charged with 32.9 g (0.26 mol) of benzyl chloride and then hermetically sealed. Subsequently, an autoclave temperature was raised under stirring from 50° C. to 70° C. over 4.5 hours, the temperature was then raised to 85° C. over 3 hours, and the reaction was performed at 85° C. for 24 hours, to obtain a reaction product. The reaction product was subjected to temperature lowering to room temperature (25° C.), and this was then dissolved in 100 mL of water and 200 mL of methanol, to prepare a solution of the reaction product. The foregoing solution was passed through a column having 200 mL of a cation exchange resin filled therein and then passed through a column having 200 mL of an anion exchange resin filled therein. Subsequently, the methanol and water were distilled off from the solution after passing through the columns, and the residue was dried under reduced pressure with a vacuum pump (0.1 mmHg) at 100° C. for 1 hour, to obtain 40 g of PAG-A1.

As for the PAG-A1, the fact that an infrared absorption spectrum (3,450 cm$^{-1}$) assigned to the hydroxyl group vanished reveals R$^2$=phenyl group.

Production Example A2

(Step A2-1)
In order to introduce a group (DSB) derived from distyrylbenzene into R$^1$, an autoclave was charged with 40 g of a compound having a hydroxyl group added to a benzene ring of trans, trans-1-styryl-4-styrylbenzene and 4.0 g of powdered sodium methoxide and then hermetically sealed. Then, an autoclave temperature was raised to 105° C., and 95 g (1.32 mol) of butylene oxide was injected into the autoclave from the liquid-introducing tube under stirring over 9 hours, to obtain a reaction product. The reaction product was subjected to temperature lowering to room temperature (25° C.), and this was then dissolved in 100 mL of water and 200 mL of methanol, to prepare a solution of the reaction product. The foregoing solution was passed through a column having 200 mL of a cation exchange resin filled therein and then passed through a column having 200 mL of an anion exchange resin filled therein, to remove the sodium ion from the reaction product. Subsequently, the methanol and water were distilled off from the solution after passing through the columns, and the residue was dried under reduced pressure with a vacuum pump (0.4 mmHg) at 100° C. for 1 hour, to obtain 110 g of a one-end blocked polyalkylene glycol-based compound A2 (R$^1$=DSB, R$^2$=H, R$^3$=butylene group (monomer:butylene oxide (BO), hereinafter also referred to as "C4"), m=6).

(Step A2-2)
The same procedures as in Step A1-2 of Production Example A1 were followed, except for changing the benzyl chloride to 10 g of distyrylbenzene chloride (compound in which a chlorine atom is added to the benzene ring of trans, trans-1-styryl-4-stylylbenzene), to obtain 180 g of PAG-A2.

From the measurement results regarding the hydroxyl value as shown in Table 1, as for the PAG-A2, it is noted that a compound of R$^2$=DSB and a compound of R$^2$=H coexist.

Production Example B1

(Step B1-1)
The same procedures as in Step A1-1 of Production Example A1 were followed, except for changing the sodium phenoxide to 3.0 g of sodium methoxide and further changing the amount of the propylene oxide to 77 g, to obtain 75 g of a one-end blocked polyalkylene glycol-based compound B1 (R$^1$=Me, R$^2$=H, R$^3$=C3, m=19).

(Step B1-2)
The same procedures as in Step A1-2 of Production Example A1 were followed, except for changing the benzyl chloride to 36.8 g of methyl iodide and further changing the reaction time at 85° C. to 6 hours, to obtain 38 g of PAG-B1.

From the measurement results regarding the hydroxyl value as shown in Table 1, as for the PAG-B1, a compound of R$^2$=Me and a compound of R$^2$=H coexist.

Production Example B2

(Step B2-1)
The same procedures as in Step A1-1 of Production Example A1 were followed, except for changing the sodium phenoxide to 2.7 g of sodium methoxide and further changing the amount of the propylene oxide to 77 g, to obtain 74 g of a one-end blocked polyalkylene glycol-based compound B2 (R$^1$=Me, R$^2$=H, R$^3$=C3, m=21).

(Step B2-2)
The same procedures as in Step A1-2 of Production Example A1 were followed, except for changing the benzyl chloride to 36.8 g of methyl iodide and further changing the reaction time at 85° C. to 1 hour, to obtain 51 g of PAG-B3.

From the measurement results regarding the hydroxyl value as shown in Table 1, as for the PAG-B3, it is noted that though a compound of R$^2$=Me and a compound of R$^2$=H coexist, the proportion at which the compound of R$^2$=Me occupies is lower than that of the PAG-B1.

Production Example B3

(Step B3-1)
The same procedures as in Step A1-1 of Production Example A1 were followed, except for changing the sodium phenoxide to 3.0 g of sodium methoxide and further changing the amounts of the ethylene oxide and the propylene oxide to 11.5 g and 61.6 g, respectively, to obtain 73 g of a one-end blocked polyalkylene glycol-based compound B3 (R$^1$=Me, R$^2$=H, R$^3$=C3+ethylene group (monomer:ethylene oxide (EO), hereinafter also referred to as "C2"), m=20).

(Step B3-2)
The same procedures as in Step A1-2 of Production Example A1 were followed, except for changing the benzyl chloride to 36.8 g of methyl iodide and further changing the reaction time at 85° C. to 6 hours, to obtain 57 g of PAG-B3.

From the measurement results regarding the hydroxyl value as shown in Table 1, as for the PAG-B3, it is noted that a compound of R$^2$=Me and a compound of R$^2$=H coexist.

Examples 1 to 2 and Comparative Examples 1 to 3

With respect to PAG-A1 to PAG-A2 and PAG-B1 to PAG-B3 synthesized in Production Examples A1 to A2 and Production Examples B1 to B3, respectively, the mass average molecular weight (Mw), the number average molecular weight (Mn), the 40° C. kinematic viscosity, the 100° C. kinematic viscosity, the viscosity index, the hydroxyl value, and the volume resistivity were measured or calculated.

<Mass Average Molecular Weight (Mw) and Number Average Molecular Weight (Mn)>

The mass average molecular weight (Mw) and the number average molecular weight (Mn) were measured by means of gel permeation chromatography (GPC). As for the GPC, the measurement was performed by using connected two columns: TSKgel Super Multipore HZ-M, manufactured by Tosoh Corporation, using tetrahydrofuran as an eluent, and using a reflective index detector as a detector, thereby determining the mass average molecular weight (Mw) and the number average molecular weight (Mn) while using polystyrene as a standard sample.

<40° C. Kinematic Viscosity, 100° C. Kinematic Viscosity, and Viscosity Index>

The 40° C. kinematic viscosity and the 100° C. kinematic viscosity of the polyalkylene glycol-based compound were measured using a glass-made capillary viscometer in conformity with JIS K2283-2000, thereby calculating the viscosity index of the polyalkylene glycol-based compound.

<Hydroxyl Value>

Measured by the neutralization titration method in conformity with JIS K0070.

<Volume Resistivity>

Measured at room temperature (25° C.) in conformity with JIS C2101-24 (volume resistivity test).

The case where the volume resistivity is 0.0030 TΩ·m or more was designated as "acceptance" (evaluation A), whereas the case where the volume resistivity is less than 0.0030 TΩ·m was designated as "fail" (evaluation F).

The results are shown in Table 1. The numerical value of $R^3$ in Table 1 is a proportion (molar ratio) of each of the components (C2, C3, and C4) relative to the total amount (100) of C2, C3, and C4.

TABLE 1

|  |  | Example 1 | Example 2 | Comparative Example 1 |
|---|---|---|---|---|
| Kind of PAG |  | PAG-A1 | PAG-A2 | PAG-B1 |
| $R^1$ |  | Phenyl group | DSB | Me |
| $R^2$ |  | Phenyl group | DSB, H | Me, H |
| $R^3$ | C2 (EO) | 0 | 0 | 0 |
|  | C3 (PO) | 100 | 0 | 100 |
|  | C4 (BO) | 0 | 100 | 0 |
| m |  | 16 | 6 | 19 |
| Mass average molecular weight (Mw) |  | 1100 | 1200 | 1200 |
| Number average molecular weight (Mn) |  | 1000 | 1000 | 1100 |
| 40° C. kinematic viscosity | mm²/s | 61.26 | 312.8 | 50.24 |
| 100° C. kinematic viscosity | mm²/s | 11.61 | 21.59 | 10.5 |
| Viscosity index |  | 188 | 82 | 205 |
| Hydroxyl value | mgKOH/g | 6.9 | 53.9 | 5.0 |
| Volume resistivity (at 25° C.) | TΩ·m | 0.0033 | 0.1400 | 0.0020 |
| Evaluation of volume resistivity |  | A | A | F |

|  |  | Comparative Example 2 | Comparative Example 3 |
|---|---|---|---|
| Kind of PAG |  | PAG-B2 | PAG-B3 |
| $R^1$ |  | Me | Me |
| $R^2$ |  | Me, H | Me, H |
| $R^3$ | C2 (EO) | 0 | 20 |
|  | C3 (PO) | 100 | 80 |
|  | C4 (BO) | 0 | 0 |
| m |  | 21 | 20 |
| Mass average molecular weight (Mw) |  | 1300 | 1100 |
| Number average molecular weight (Mn) |  | 1200 | 1000 |
| 40° C. kinematic viscosity | mm²/s | 57.41 | 47.00 |
| 100° C. kinematic viscosity | mm²/s | 10.89 | 10.25 |
| Viscosity index |  | 185 | 214 |
| Hydroxyl value | mgKOH/g | 48.7 | 6.2 |
| Volume resistivity (at 25° C.) | TΩ·m | 0.0010 | 0.0008 |
| Evaluation of volume resistivity |  | F | F |

The following is understood from Table 1.

In view of the fact that in all of Examples 1 to 2, the volume resistivity was 0.0030 TΩ·m or more, it is noted that all of the PAG-A1 to PAG-A2 obtained in the aforementioned Production Examples A1 to A2 are excellent in the electric insulation.

In contrast, in Comparative Examples 1 to 3, the volume resistivity was less than 0.0030 TΩ·m, and hence, it is noted that all of the PAG-B1 to PAG-B33 obtained in the aforementioned Production Examples B1 to B3 are inferior in the electric insulation.

The invention claimed is:

1. A lubricating oil composition, comprising a polyalkylene glycol-based compound represented by the formula (1):

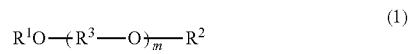

wherein $R^1$ represents a monovalent aromatic hydrocarbon group having 6 to 20 carbon atoms in one or more rings; R2 represents a monovalent aromatic hydrocarbon group having 6 to 20 carbon atoms in one or more rings or a hydrogen atom; $R^3$ represents a divalent hydrocarbon group having 2 to 4 carbon atoms; and m is a number of 1 to 40, wherein the monovalent aromatic hydrocarbon group is represented by the formula (2):

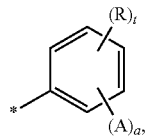

wherein (t+a)≤5,
t is an integer of 0 to 5,
a is an integer of 0 to 2, provided that at least one a is an integer of 1 or 2,
* represents a bonding position to the oxygen atom in the formula (1),
R is each independently a methyl group, an ethyl group or a vinyl group, and
A is each independently a group represented by the formula (8),

wherein z is 1,
$L^1$ is a vinylene group,
$Ar^1$ is represented by the formula (2), and
in the formula (8), when $Ar^1$ is the formula (2), R, A and t have the meaning above, and * represents a bonding position to $L^1$ in the formula (8).

2. The lubricating oil composition of claim 1, wherein the polyalkylene glycol-based compound has a hydroxyl value of 60 mgKOH/g or less.

3. The lubricating oil composition according to claim 1, further comprising at least one additive selected from the group consisting of an antioxidant, an oiliness improver, an oxygen scavenger, an extreme pressure agent, a copper deactivator, a rust inhibitor, an anti-foaming agent, and a viscosity index improver.

4. The lubricating oil composition according to claim 1, wherein m is an integer of 5 to 40.

5. The lubricating oil composition according to claim 1, wherein $R^1$ represents a group derived from distyrylbenzene, and the group derived from distyrylbenzene is a group in which in distyrylbenzene, the hydrogen atom is eliminated at a position serving as a bonding point to the oxygen atom in the formula (1).

6. The lubricating oil composition according to claim 1, wherein $R^2$ represents a hydrogen atom or a group derived from distyrylbenzene, and the group derived from distyrylbenzene is a group in which in distyrylbenzene, the hydrogen atom is eliminated at a position serving as a bonding point to the oxygen atom in the formula (1).

7. The lubricating oil composition according to claim 1, wherein $R^1$ represents a group derived from distyrylbenzene, $R^2$ represents a hydrogen atom or a group derived from distyrylbenzene, and the group derived from distyrylbenzene is a group in which in distyrylbenzene, the hydrogen atom is eliminated at a position serving as a bonding point to the oxygen atom in the formula (1).

8. The lubricating oil composition according to claim 1, wherein m is an integer of 5 to 35.

9. The lubricating oil composition according to claim 1, wherein m is an integer of 5 to 20.

10. The lubricating oil composition of claim 1, wherein the polyalkylene glycol-based compound has a hydroxyl value of 40 mgKOH/g or less.

11. The lubricating oil composition of claim 1, wherein the polyalkylene glycol-based compound has a hydroxyl value of 20 mgKOH/g or less.

12. The lubricating oil composition of claim 1, wherein the polyalkylene glycol-based compound has a mass average molecular weight of 500 to 5000.

13. The lubricating oil composition of claim 1, wherein the polyalkylene glycol-based compound has a mass average molecular weight of 700 to 3000.

14. The lubricating oil composition of claim 1, wherein the polyalkylene glycol-based compound has a number average molecular weight of 500 to 5000.

15. The lubricating oil composition of claim 1, wherein the polyalkylene glycol-based compound has a number average molecular weight of 600 to 2500.

16. The lubricating oil composition of claim 1, wherein the polyalkylene glycol-based compound has a 40° C. kinematic viscosity of 10 to 400 mm²/s.

17. The lubricating oil composition of claim 1, wherein the polyalkylene glycol-based compound has a 100° C. kinematic viscosity of 2.0 to 30 mm²/s.

18. The lubricating oil composition of claim 1, wherein the polyalkylene glycol-based compound has a viscosity index of 70 to 250.

19. The lubricating oil composition of claim 1, wherein the polyalkylene glycol-based compound is 50% to 100% by mass based on a total weight of the lubricating oil composition.

20. The lubricating oil composition of claim 1, wherein the polyalkylene glycol-based compound is 70% to 100% by mass based on a total weight of the lubricating oil composition.

* * * * *